US009545220B2

United States Patent
Sidlesky

(10) Patent No.: US 9,545,220 B2
(45) Date of Patent: Jan. 17, 2017

(54) ENDOSCOPIC MEASUREMENT SYSTEM AND METHOD

(71) Applicant: V.T.M (VIRTUAL TAPE MEASURE) TECHNOLOGIES LTD., Atlit (IL)

(72) Inventor: Avishay Sidlesky, Atlit (IL)

(73) Assignee: V.T.M (Virtual Tape Measure) Technologies Ltd., Atlit (IL)

( * ) Notice: Subject to any disclaimer, the term of this patent is extended or adjusted under 35 U.S.C. 154(b) by 0 days.

(21) Appl. No.: 15/037,603

(22) PCT Filed: Feb. 25, 2015

(86) PCT No.: PCT/IL2015/050211
§ 371 (c)(1),
(2) Date: May 18, 2016

(87) PCT Pub. No.: WO2015/132778
PCT Pub. Date: Sep. 11, 2015

(65) Prior Publication Data
US 2016/0287141 A1    Oct. 6, 2016

Related U.S. Application Data

(60) Provisional application No. 61/946,841, filed on Mar. 2, 2014.

(51) Int. Cl.
*A61B 1/06* (2006.01)
*A61B 5/107* (2006.01)
(Continued)

(52) U.S. Cl.
CPC ........... *A61B 5/1076* (2013.01); *A61B 5/0073* (2013.01); *A61B 5/0084* (2013.01); *A61B 5/1079* (2013.01);
(Continued)

(58) Field of Classification Search
CPC ................ A61B 5/1076; A61B 1/06
See application file for complete search history.

(56) References Cited

U.S. PATENT DOCUMENTS 5,090,400 A    2/1992    Saito
5,109,276 A *  4/1992    Nudelman ......... A61B 1/00193
                                                257/E31.115
(Continued)

FOREIGN PATENT DOCUMENTS

CN    2689888 Y    4/2005
EP    2106748 A1    10/2009
(Continued)

OTHER PUBLICATIONS

Buschinelli et al., Optical Profilometer Using Laser Based Conical Triangulation for Inspection of Inner Geometry of Corroded Pipes in Cylindrical Coordinates, Proceedings of the SPIE—The International Society for Optical Enginerring, vol. 8788, pp. 87881H (2013) (11 pages).
(Continued)

*Primary Examiner* — Jay Patel
*Assistant Examiner* — Irfan Habib
(74) *Attorney, Agent, or Firm* — Roach Brown McCarthy & Gruber, P.C.; Kevin D. McCarthy

(57) ABSTRACT

The invention is a system and method for measuring 3D distances and dimensions of objects in endoscopic images by using a light plane to make Euclidean and geodesic measurements. The endoscopic measurement system of the invention comprises a flexible or rigid endoscopic device equipped with standard visualization means and a module containing components for generating a light plane. Based on triangulation, the intersection curve between the light lane and the object of interest is measurable in 3D in the coordinate system of the visualization means.

20 Claims, 3 Drawing Sheets

(51) Int. Cl.
*A61B 5/00* (2006.01)
*G02B 23/24* (2006.01)
*G06T 7/00* (2006.01)
*G02B 27/09* (2006.01)

(52) U.S. Cl.
CPC ....... *G02B 23/2415* (2013.01); *G02B 23/2461* (2013.01); *G02B 23/2484* (2013.01); *G06T 7/004* (2013.01); *G06T 7/0012* (2013.01); *A61B 1/06* (2013.01); *A61B 2562/028* (2013.01); *A61B 2576/00* (2013.01); *G02B 27/09* (2013.01); *G06T 2207/10068* (2013.01)

(56) References Cited

U.S. PATENT DOCUMENTS

| | | | | |
|---|---|---|---|---|
| 5,436,655 A * | 7/1995 | Hiyama | A61B 1/063 | 348/139 |
| 5,437,290 A * | 8/1995 | Bolger | A61B 5/1076 | 128/898 |
| 5,784,098 A * | 7/1998 | Shoji | G01B 11/25 | 348/139 |
| 5,920,319 A * | 7/1999 | Vining | A61B 5/1076 | 345/419 |
| 5,950,629 A * | 9/1999 | Taylor | A61B 34/20 | 128/897 |
| 6,009,189 A * | 12/1999 | Schaack | A61B 1/00147 | 348/137 |
| 6,059,718 A * | 5/2000 | Taniguchi | A61B 1/0005 | 600/117 |
| 6,063,023 A * | 5/2000 | Sakiyama | A61B 1/00193 | 600/117 |
| 6,135,946 A * | 10/2000 | Konen | A61B 1/005 | 600/117 |
| 6,459,481 B1 * | 10/2002 | Schaack | A61B 5/1076 | 356/241.1 |
| 6,470,205 B2 * | 10/2002 | Bosselmann | A61B 34/70 | 600/424 |
| 6,482,148 B1 * | 11/2002 | Luke | A61B 1/00183 | 600/117 |
| 6,546,277 B1 * | 4/2003 | Franck | A61B 90/10 | 600/426 |
| 6,613,002 B1 * | 9/2003 | Clark | A61B 5/1076 | 600/104 |
| 7,385,708 B2 | 6/2008 | Ackerman et al. | | |
| 7,740,578 B2 | 6/2010 | Little | | |
| 7,824,328 B2 * | 11/2010 | Gattani | A61B 1/0005 | 600/117 |
| 7,945,310 B2 * | 5/2011 | Gattani | A61B 1/00039 | 600/117 |
| 7,967,743 B2 * | 6/2011 | Ishihara | A61B 1/043 | 600/103 |
| 8,248,414 B2 * | 8/2012 | Gattani | A61B 1/00009 | 345/424 |
| 8,248,465 B2 | 8/2012 | Doi | | |
| 8,465,415 B2 | 6/2013 | Ogawa | | |
| 8,496,575 B2 | 7/2013 | Doi | | |
| 8,558,879 B2 | 10/2013 | Doi | | |
| 8,614,768 B2 * | 12/2013 | Jacobsen | A61B 1/05 | 348/379 |
| 8,690,762 B2 * | 4/2014 | Jacobsen | A61B 1/00177 | 600/116 |
| 8,717,428 B2 * | 5/2014 | Jacobsen | A61B 1/05 | 348/68 |
| 8,795,157 B1 * | 8/2014 | Yaron | A61B 1/00193 | 348/65 |
| 8,828,028 B2 * | 9/2014 | Jacobsen | A61B 1/00154 | 600/109 |
| 8,845,526 B2 * | 9/2014 | Hart | A61B 1/00082 | 356/626 |
| 9,060,704 B2 * | 6/2015 | Jacobsen | A61B 1/00096 | |
| 9,119,552 B2 * | 9/2015 | Baumann | A61B 1/06 | |
| 9,144,664 B2 * | 9/2015 | Jacobsen | A61B 1/05 | |
| 9,157,728 B2 * | 10/2015 | Ogawa | A61B 5/6885 | |
| 9,247,865 B2 * | 2/2016 | Igarashi | A61B 1/042 | |
| 9,259,142 B2 * | 2/2016 | Jacobsen | A61B 1/00188 | |
| 2002/0158870 A1 * | 10/2002 | Brunkhart | G01B 11/002 | 345/424 |
| 2003/0029464 A1 * | 2/2003 | Chen | A61B 90/36 | 600/429 |
| 2004/0242961 A1 | 12/2004 | Bughici et al. | | |
| 2005/0182295 A1 * | 8/2005 | Soper | A61B 1/0008 | 600/117 |
| 2007/0013710 A1 * | 1/2007 | Higgins | A61B 1/00147 | 345/581 |
| 2007/0061726 A1 * | 3/2007 | Rahn | G06F 3/04845 | 715/719 |
| 2008/0071141 A1 * | 3/2008 | Gattani | A61B 1/0005 | 600/117 |
| 2008/0071142 A1 * | 3/2008 | Gattani | A61B 1/0005 | 600/117 |
| 2009/0063118 A1 * | 3/2009 | Dachille | G06F 17/30262 | 703/11 |
| 2009/0225321 A1 | 9/2009 | Bendall et al. | | |
| 2012/0289778 A1 | 11/2012 | Chan | | |
| 2014/0028819 A1 | 1/2014 | Nakano | | |
| 2014/0357988 A1 * | 12/2014 | Grass | G01T 1/161 | 600/424 |
| 2016/0205387 A1 * | 7/2016 | Kasumi | G09G 5/00 | 348/53 |

FOREIGN PATENT DOCUMENTS

| | | |
|---|---|---|
| EP | 2160974 A1 | 3/2010 |
| EP | 2630915 A1 | 8/2013 |
| WO | 01/80734 A1 | 11/2001 |
| WO | 2005/027739 A1 | 3/2005 |
| WO | 2012/147679 A1 | 11/2012 |

OTHER PUBLICATIONS

International Search Report from a counterpart foreign application—PCT/IL2015/050211—mailed Jun. 10, 2015; 4 pages.
Written Opinion of the International Searching Authority from a counterpart foreign application—PCT/IL2015/050211—mailed Jun. 10, 2015; 4 pages.
Wurzbacher et al., Calibration of laryngeal endoscopic high-speed image sequences by an automated detection of a parallel laser line projections, Medical Image Analysis 12 (2008) 300-317 (18 pages).
Kral et al., Proof-of-concept of a laser mounted endoscope for touch-less navigated procedures, Lasers Surg Med. Aug. 2013; 45(6): 377-382—9 pages.
Depth-kymography: high-speed calibrated 3D imaging of human vocal fold vibration dynamics' by N. A. George et al., Phys. Med. Biol. 53 (2008) 2667-2675.

* cited by examiner

ENDOSCOPIC MEASUREMENT SYSTEM AND METHOD

FIELD OF THE INVENTION

The invention is from the field of endoscopes, borescopes and similar devices, whether medical or industrial. Specifically the invention relates to systems for performing accurate three-dimensional measurement of the dimensions of objects viewed with camera equipped endoscopes, laparoscopes, catheters, borescopes, and other flexible, semi-flexible, semi-rigid or rigid similar instruments.

BACKGROUND OF THE INVENTION

When using a camera equipped borescope to inspect engines or machined parts for imperfections of interior surfaces, it would be advantageous to be able to perform and record accurate, three-dimensional measurements to obtain the dimensions of the imperfections in order to be able to evaluate the extent of the damage and to determine what corrective measures should be taken.

During endoscopic medical procedures, it is of an advantage to perform accurate three dimensional measurements to obtain dimensions of anatomical structures within the lumen, such as lesions, stenoses, tumors, and the like. Tracking such measurements along time may further improve the level of care provided.

For example, Otorhinolaryngologists may benefit from recording the dimensions, opening, and alignment of patients' vocal cords. Pulmonologists can quantify airway size and establish treatment protocol accordingly. Monitoring these data provides valuable information related to effectiveness of a treatment, disease progression and the like. Another example is monitoring the size of polyps in the gastrointestinal tract or the stomach, to support further treatment decisions.

Currently, physicians using a state of the art endoscope, be it flexible or rigid, monocular or stereoscopic, do not have a true volumetric perspective within the acquired image and are unable to conduct accurate measurements. A common practice is to place an object of known size (e.g., a catheter with known diameter) next to the anatomical structure and use it as a scale to assess dimensions.

The actual necessity of obtaining accurate 3D measurements during endoscopic procedures is manifested by several patents and patent applications, describing inventions aimed at providing a solution to the problem. Some of these patents and applications are registered to key vendors in the medical devices arena, such as Olympus, Toshiba, Covidien and others. Most of the state of the art (issued patents and applications) attempts to obtain a full depth image of the endoscopic field of view. Additionally, several vendors are promoting stereoscopic endoscopy to answer complementary needs.

In U.S. Pat. No. 5,090,400, 'Measuring Endoscope', issued to Toshiba on Feb. 25 1992, the use of a laser pattern generated at the end of a fiber by a standard diffraction grating is synchronized with the illumination light for observation.

In U.S. Pat. No. 5,784,098, 'Apparatus for Measuring Three-dimensional Configurations', issued to Olympus on Jul. 21 1998, an oscillating structured light and beam splitters are used to measure the 3D configuration of an object.

In U.S. Pat. No. 8,248,465, 'Measuring Endoscope Apparatus and Program', issued to Olympus on Aug. 21 2012, two images combined with triangulation on image data is used to generate the measurements.

In U.S. Pat. No. 8,496,575, 'Measuring Endoscope Apparatus, Program and Recording Medium', issued to Olympus on Jul. 30 2013, a system that includes an endoscope and a processing section that measures distances on two images received from the endoscope based on a triangulation method.

U.S. Pat. No. 8,558,879, 'Endoscope Apparatus and Measurement Method', issued to Olympus on Oct. 15 2013, further describes an apparatus and method, which is partly manual in nature, requiring the user to mark correspondence points in both images.

U.S. Pat. No. 8,465,415, 'Endoscope Apparatus and Measurement Method', issued to Olympus on Jun. 18 2013, takes a different approach, by measuring a shake in an interlaced image to generate a second image that is measurable.

There are yet other approaches to providing a solution to the problem, for example:

In U.S. Pat. No. 7,740,578, 'Direct reading endoscopic measuring instrument and method', issued to Paul K. Little on Jun. 22 2010, the invention relates to a physical reticule which is extended from the distal end of the endoscope and placed proximate to an anatomical structure to be measured, and then retracted accordingly.

In CN 2,689,888Y, 'Measuring type endoscope biopsy forceps', Apr. 6 2005, the inventors use color coded graduation marks to assess the extent of disease.

Additional background information may be found in the following patent applications: US2004/0242961 (corresponding to EP1480067A1), US2009/0225321, US2012/0289778, US2014/0028819, WO2005/027739A1, WO2012/147679A1, EP2106748A1, EP2160974A1, EP2630915A1 and in a paper published in 'Lasers in Surgery and Medicine 45:377-382 (2013—http://www.ncbi.nlm.nih.gov/pmc/articles/PMC3791553/)', titled 'Proof-of-concept of a Laser Mounted Endoscope for Touch-Less Navigated Procedures', which emphasizes the need for measuring 3D data in adjacent domains.

Further research includes 'Calibration of laryngeal endoscopic high-speed image sequences by an automated detection of parallel laser line projections' by T. Wurzbacher et al., Medical Image Analysis 12 (2008) 300-317, where two parallel planes of known distance, mounted on a rigid endoscope, generate two intersection curves with the vocal cords that are approximated as straight lines, and are merely used for coarse scaling of image pixels. Another research article titled 'Depth-kymography: high-speed calibrated 3D imaging of human vocal fold vibration dynamics' by N. A. George et al., Phys. Med. Biol. 53 (2008) 2667-2675, describes a rigid endoscope equipped with a laser projection channel that uses a large triangulation angle and a specific calibration method to enable highly accurate vertical measurement of the front surface of the vocal folds, as they vibrate in low amplitude. Both of these setups are inapplicable for measuring lumens with a large depth of field, and therefore are unsuitable for providing 3D measurements in general.

To the best of the inventor's knowledge, no commercially available medical endoscope to date has the capability to accurately take 3D measurements and to record them. Furthermore, the state of the art solutions for three-dimensional endoscopy are mostly complex. In some, the device includes a complex assembly of mechanical, electrical and optical components. In others, such as Olympus iPLEX stereoscopic borescope, the measured object must have salient features and the required extra user interaction renders the process cumbersome.

It is noted that the terms "endoscope" and "endoscopic device" are used herein in a generic sense to apply to endoscopes, catheters, laparoscopes, and similar instruments used in medical applications and also to borescopes and similar instruments used in non-medical applications.

It is therefore a purpose of the present invention to provide a system and a method capable of making accurate 3D measurements of objects observed in the field of view of an endoscopic visualization system.

It is another purpose of the present invention to provide systems capable of making accurate 3D measurements of objects observed in the field of view of an endoscopic visualization system that is structurally much less complex than existing systems.

It is another purpose of the present invention to provide a method capable of making accurate 3D measurements of objects observed in the field of view of an endoscopic visualization system that is structurally much less cumbersome to carry out than existing methods.

Further purposes and advantages of this invention will appear as the description proceeds.

SUMMARY OF THE INVENTION

In a first aspect the invention is a system for measuring 3D distances and dimensions of objects that are visible in endoscopic images. The system comprises:
  a. a flexible or rigid endoscopic device comprising visualization means;
  b. a conventional endoscopy system adapted to operate the endoscopic device and to obtain and display images gathered by the visualization means;
  c. a light plane generating module comprising a light source and optical elements configured to generate a light plane; and
  d. a processing station comprising: processing means, dedicated software modules adapted for making both Euclidian and geodesic measurements, a graphical user interface (GUI), software, a pointing device, and a display adapted to present to the user of the system images acquired by the visualization means overlaid with graphics and text.

In embodiments of the system of the invention some or all components of the processing station are integrated into the conventional endoscopy system.

Embodiments of the system of the invention comprise a docking station for calibration of at least one of projection parameters of the visualization means, distortions of the visualization means and light plane parameters.

In embodiments of the system of the invention the dedicated software modules comprise programs that automatically perform at least one of the following operations:
  a. assigning 3D coordinates to each pixel along the intersection curves of the light plane with the object;
  b. making Euclidean and geodesic measurements between at least two points overlaid by the user on an image displayed on the display;
  c. providing and displaying measurements of the Euclidean distance of gaps or diameters of holes and making geodesic measurements of curve segments to determine the diameter of objects seen in the images according to preprogrammed requests of the user or by pointing at a single point on the screen; and
  d. determining the projection parameters and distortions of the visualization means and light plane parameters from images recorded during a calibration process.

In embodiments of the system of the invention the light plane generating module comprises one of the following:
  a. a light source and a single lens;
  b. a light source and an optical arrangement comprising at least one lens;
  c. a light source and a diffractive optical element (DOE);
  d. a light source and an optical arrangement comprising at least one DOE;
  e. a light source positioned at the proximal end of an optical fiber leading to a diffraction grating at the distal tip of the endoscope; and
  f. a light source positioned at the proximal end of an optical fiber leading to a lens at the distal tip of the endoscope.

In embodiments of the system of the invention the light source is one of:
  a. a laser diode;
  b. a LED; and
  c. a light source that produces colored light.

In embodiments of the system of the invention the light plane generating module is integrated in a specific design for a dedicated depth measuring endoscopic device.

In embodiments of the system of the invention the light plane generating module is a separate measurement device that can be mounted as an add-on to an existing, regular flexible or rigid endoscopic device.

In embodiments of the system of the invention the light plane generating module is mounted on the endoscopic device in one of the following ways:
  a. in a working channel of the endoscopic device; and
  b. in one channel of a two channel sheath wherein the insertion section of the endoscopic device is slid into the other channel; and
  c. a clip or a band attached to the outside of the distal tip of the endoscopic device.

In embodiments of the system of the invention the light plane generating module is mounted below the objective lens of the visualization means in a pivoting arm configured to allow the distance between the focal point of the visualization means and the light plane to be changed.

Embodiments of the system of the invention comprise at least one of:
  a. In embodiments of the system of the invention In embodiments of the system of the invention multiple light planes;
  b. light planes having different line patterns or color coding.

Embodiments of the system of the invention comprise at least one of:
  a. a single light plane that is rotated or swept manually; and
  b. a single light plane that is rotated or swept in sync with an image acquisition camera.

In these embodiments rotation or sweep is achieved by one of:
  a. MEMS mirrors;
  b. a rotation mechanism; and
  c. a combination of MEMS mirrors and a rotation mechanism.

In embodiments of the system of the invention a reticle is superimposed on images from the visualization means displayed on the display.

In a second aspect the invention is a method for measuring 3D distances and dimensions of objects that are visible in endoscopic images, the method comprising the following steps:
 a. supplying a system according to claim 1;
 b. for a non-integrated add-on light plane generating module, mounting the light plane generating module at the tip of the endoscopic device;
 c. for an integrated or a non-integrated add-on light plane generating module, manipulating the endoscopic device such that the light plane coincides with the object to be measured;
 d. acquiring an image;
 e. repeating steps c and d for additional images if desired;
 f. selecting an image to be analyzed and using the GUI software to mark at least two points on the intersection curves of the light plane with the object;
 g. using the dedicated software module to measure and display the Euclidian distances between the marked points and, if the points lie on the same curve segment, to measure the geodesic distances along the segment;
 h. repeating steps f and g to measure additional objects if desired;
 i. recording the measurement data and related overlaid graphics if desired; and
 j. repeating steps f, g, h, and i for additional images.

In embodiments of the method of the invention in step f only one point is marked on the image and step g further provides and displays measurements of the Euclidean distance of gaps or diameters of holes and geodesic measurements of curve segments to determine the diameter of objects seen in the images. In some of these embodiments the curve segments are displayed in a separate view, thereby generating a non-distorted quantitative profile of the tubular objects in the endoscopic view and, for cases where in step c the light plane is aligned with the longitudinal axis of a tubular object, the longitudinal cross-section profile of the tubular object is provided. In some of these embodiments steps d and e are replaced with on-line real-time automatic processing of video input during the procedure.

In embodiments of the method of the invention in step f curve segments or gaps are automatically identified and analyzed by the dedicated software module of the processing station and in step g the resulting measurements are displayed automatically, thereby automatically measuring geodesic lengths or diameters of features or gaps or diameters of holes.

In embodiments of the method of the invention steps f to j are performed off-line after the procedure has been completed or on-line on the recently acquired image during the procedure.

In embodiments of the method of the invention a spray of water, saline vapor, or the like is used to create haze to enable visualization of the laser plane.

In embodiments of the method of the invention the calibration in step b is automatically performed by inserting the tip of the endoscopic device into a calibration docking station.

All the above and other characteristics and advantages of the invention will be further understood through the following illustrative and non-limitative description of embodiments thereof, with reference to the appended drawings.

DETAILED DESCRIPTION OF EMBODIMENTS OF THE INVENTION

The current invention takes a simplified approach to solving the problem of measuring 3D distances and dimensions of objects in endoscopic images by using a light plane to make linear and geodesic measurements. The endoscopic measurement system of the invention comprises a flexible or rigid endoscopic device equipped with standard endoscopic visualization means, e.g. a camera, a processing station and components for generating a light plane. Based on triangulation, the intersection curve in an endoscopic image between the light plane and the object of interest is measurable in 3D in the camera coordinate system, much like using a virtual measuring tape.

To the best of the inventor's knowledge, this concept has not been adapted to conduct generic quantitative endoscopic measurements in 3D in a human body and in other lumens.

Figure 1:
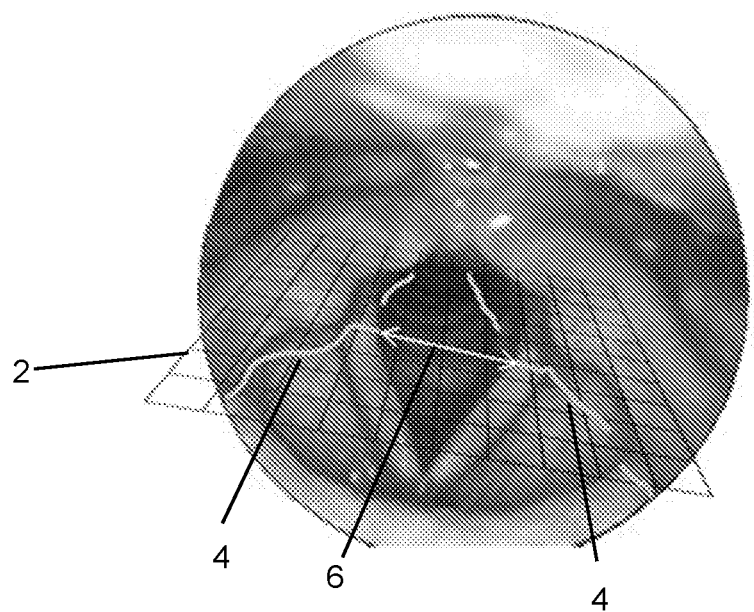
FIG. 1 shows an image of a human larynx imaged using a standard endoscopic visualization system with superimposed features pertaining to the light plane.

FIG. 1 shows an image of a human larynx imaged using a standard endoscope. Laryngology constitutes a significant clinical application where measurements are required, as aforementioned in the background section. In this image the light plane, represented by a superimposed reticle 2, the intersection curves of the light plane with the larynx 4, and a measurement of the opening of the vocal cords 6 are schematically illustrated.

Figure 2:
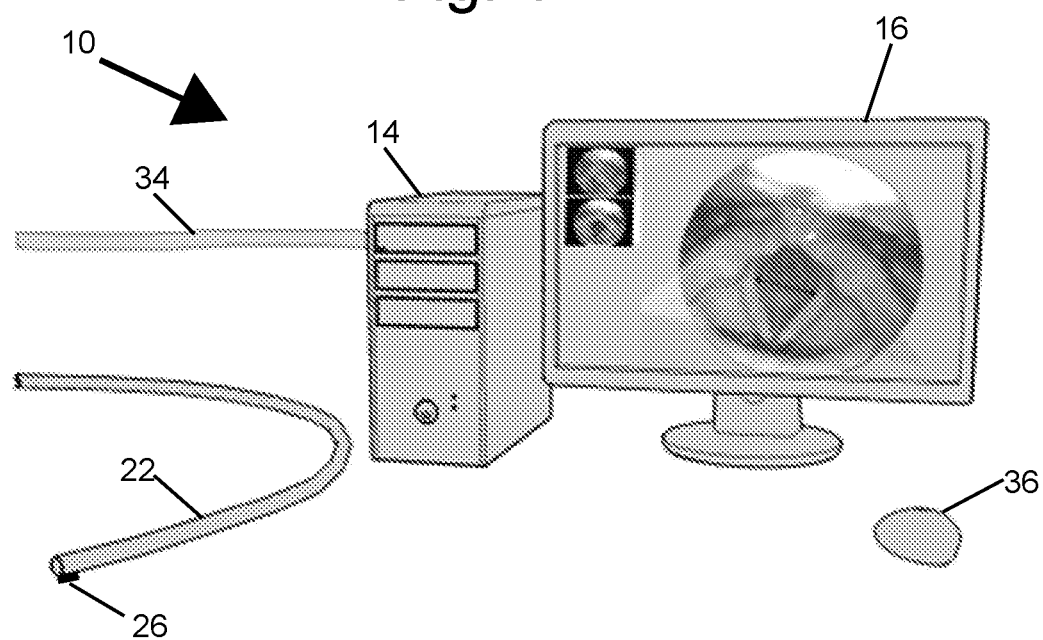
FIG. 2 is a schematic illustration of a specific embodiment of the system of the invention in which a separate processing station is included.

FIG. 2 is a schematic illustration of a specific embodiment of the system of the invention in which a separate processing station is included. The system comprises an endoscopic device that comprises standard endoscopic visualization means (e.g. a camera) and a light plane generating module 12 attached to the distal end of the endoscopic device 22 and a processing station 10 comprising processing means 14 that acquires the images from the conventional endoscopy system used to operate the endoscope, and a display 16. Processing means 14 can be, for example, a PC or laptop computer or a Field-Programmable Gate Array or Digital Signal Processor microcontroller. Processing means 14 comprises a dedicated software module that assigns 3D coordinates to each pixel along the intersection curves, a pointing device, and an additional software module implementing a GUI for taking both Euclidian and geodesic measurements at user specified locations. Display 16 presents the images, overlaid graphics and text to the user of the system. The additional software module includes an automatic mode to measure holes or gaps or the diameter of polyps either automatically detected or pointed at by the user on an image displayed on display 16. Also shown in FIG. 2 as components of processing station 10 are cable 34 that transfers images from the conventional endoscopy system connected to the endoscopic device to the processing means 14 and mouse 36, that symbolically represents the pointing device and input means for user input to the processing station.

It is noted that in other embodiments some or all of the components of processing station 10 need not be dedicated items but can be part of the conventional endoscopy system or their functions can be performed by components of the conventional endoscopy system. The embodiment of the processing station 10 in which all components are integrated into the conventional endoscopy system is referred to as a complete endoscopy suite, which is capable of conducting both conventional endoscopic procedures and performing 3D measurements according to the method of the invention.

The light plane can be generated in a number of different ways that are well known in the art. For example, a laser line module, e.g. a laser diode coupled with a single lens, an optical system comprising at least one lens, a diffractive optical element (DOE), or an optical system comprising at least one DOE, can be mounted at the distal end of the endoscopic device or a light source can be positioned at the proximal end of an optical fiber leading to either a diffraction grating or lens at the distal tip of the endoscopic device. It is noted that the light plane need not be comprised of coherent light so any light source that produces colored light, e.g. colored LEDs, can be used as a light source instead of a laser. A source producing colored light is used in order to be able to see the light plane and its intersection with features in the image against the background of the illumination light used to produce the images, which is normally white light. It is noted however that special techniques can be used that would enable the use of a white light source to produce the light plane.

The light plane generating module may be integrated in a specific design of an endoscopic device to produce a dedicated visualization, distance, and depth measuring instrument. Alternatively, the light plane generating module can be designed as a separate unit that can be mounted as an add-on to an existing, regular flexible or rigid endoscopic device.

FIG. 3 to FIG. 6 schematically show alternative ways in which the light plane generating module can be attached to an endoscopic device.

Figures 3, 4:
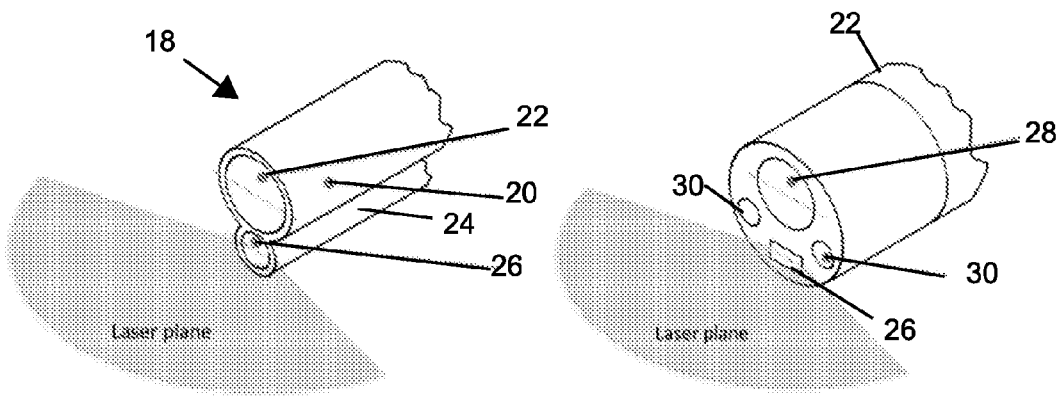
FIG. 3 to FIG. 6 schematically show alternative ways in which a light plane generating module can be attached to an endoscopic device.

FIG. 3 shows a two channel sheath 18. The insertion section 22 of the endoscopic device is slid into the upper channel 20 of sheath 18 and the light plane generating module 26 is slid into the lower channel 24 of sheath 18. If the endoscopic device comprises an available working channel, then a similar configuration is obtained, without the use of a sheath, by sliding the light plane generating module through the working channel.

FIG. 4 shows a light plane generating module 26 permanently installed at the distal end of insertion section 22 of an endoscopic device. Also shown in FIG. 4 are the visualization systems objective lens 28 and two LEDs 30 that provide illumination for capturing images with the visualization system.

Figures 5A, 5B:
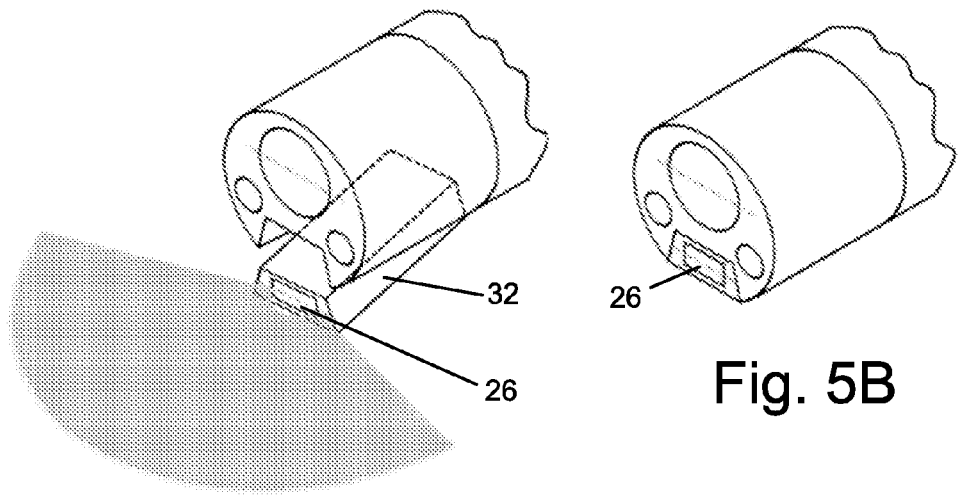

FIG. 5A and FIG. 5B show an embodiment in which the light plane generating module 26 is mounted below the objective lens in a pivoting arm 32, which allows the distance between the visualization system's focal point and the light plane to be changed for improved accuracy increasing the triangulation angle.

Another way in which the light plane generating module can be attached to the distal tip of an endoscopic device is with a clip or band. This method is especially useful for use with disposable light plane generating modules that are powered by battery.

Figure 6:
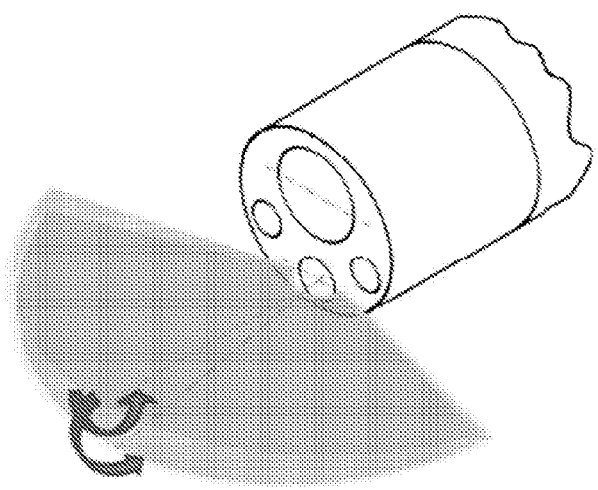

In other embodiments multiple light planes may exist, having different line patterns or color coding. In other embodiments a single light plane may be rotated or swept, such as schematically shown in FIG. 6. The rotation may be manual, providing extra flexibility to the user in measuring an anatomical structure without manipulating the endoscope, or in sync with an image acquisition camera, to enable 3D reconstruction of that anatomical structure. Fast rotation or sweep may be achieved by a MEMS mirrors or by a rotation mechanism, or any combination thereof.

Based on triangulation and with proper calibration, the 3D coordinates of the pixels along the intersection curves in the endoscopic images may be extracted since the light plane is fired at a known position and orientation relative to the focal point and primary view direction of the visualization system.

Calibrations done to find camera projection parameters and to counter distortions are well known in the art, and so are techniques to automate the process. Most commonly, a planar calibration pattern of known dimensions is sequentially imaged from several distances and directions, enabling the calculation of intrinsic/extrinsic camera parameters [Z. Zhang. "A Flexible New Technique for Camera Calibration." IEEE Transactions on Pattern Analysis and Machine Intelligence, 22(11):1330-1334, 2000].

In the system of the invention the same calibration process used to find the projection parameters and distortions of the visualization means is also used to calculate the parameters of the light plane, which appears as lines on the images of the planar calibration pattern. Once the visualization system distortions are accounted for, a plane that best fits the lines may be calculated, e.g., by least squares fitting.

Figure 7:
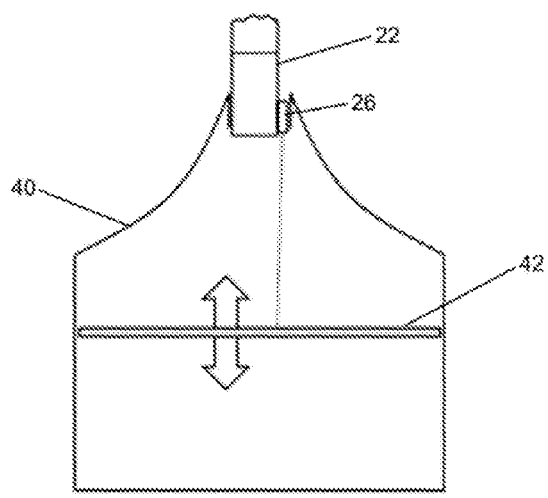
FIG. 7 schematically shows a docking station for use in calibrating the endoscopic device and light plane generating module.

In one embodiment of the system of the invention, a docking station for calibration, schematically shown in FIG. 7, is provided. Docking station 40 is used in the following way: first the user mounts the light plane generating module 26 on the distal end of the insertion section 22 of the endoscopic device. He then places the tip of the endoscopic device in the docking station 40. A mechanism (not shown) is then activated to automatically move a calibration pattern 42 up and down as shown by the arrows while capturing images that are sent automatically to the system processing means 14 where dedicated software automatically determines the calibration parameters to be applied to subsequent images taken with the endoscopic visualization means after the device is removed from the docking station.

Since the light plane parameters in the visualization means' coordinate system are known, a reticle may be superimposed on the computer screen to facilitate quick assessment of distances, including depth, diameters and the like. The reticle can be of the form of grid lines in perspective view, as depicted in FIG. 1. If the image display is not rectified to account for the visualization means' distortions, the reticle is warped accordingly. In embodiments where the light plane is rigidly positioned with respect to the objective lens, the reticle may be added along the visualization means' optical path, thus enabling a standalone hardware solution for assessment of measurements.

Optionally, a spray of water or saline vapor, and the like, may be used to create haze to enable visualization of the laser plane, as in FIG. 1. Visualizing the plane assists in the perception of depth, either instead or in conjunction with a reticle on screen.

Typically, a user of the system of the invention performs the following steps:

1. For a non-integrated add-on light plane generating module, mount the light plane generating module at the tip of the endoscopic device, insert the tip of the endoscopic device in the calibration docking station and perform automatic calibration.
2. Manipulate the endoscopic device, such that the light plane coincides with the structure to be measured.
3. Acquire the image by the dedicated software module, and repeat steps 2 and 3 for additional measurements. The light plane generating module may be turned off between measurements enabling the endoscopic procedure to be performed as usual.
4. Select an image to be analyzed and use the GUI software module to mark two points or more on the intersection curves of the light plane with the structure to be measured. The Euclidian distance between the marked points may always be automatically calculated and displayed by the GUI software module. If the points lie on the same curve segment, the geodesic distance along this segment may also be calculated and displayed.
5. Alternatively, some measurements may be provided automatically according to a preprogrammed request of the user or by pointing at a single point on the screen, such as displaying the Euclidean distance of gaps or for measuring diameters of holes, and calculating the diameter of a polyp by marking the curve on its circumference.
6. Repeat steps 4 and 5 to measure additional features.
7. The measurement data and related overlaid graphics may be recorded, and steps 4, 5, 6, and 7 may be repeated for additional images.

Steps 4, 5, 6, and 7 may be done either off-line after the procedure has been completed or on-line on the recently acquired image during the procedure.

For a dedicated endoscopic device with a fully integrated light plane generating module, the calibration has been done by the manufacturer and the method starts with step 2 and continues exactly as described above.

In an alternative embodiment, the light plane is independently manipulated in step 2 above.

Acquiring successive images visualizing intersection curves of a single plane of light in each image suffices for conducting measurements of anatomical structures.

An additional example of the use of the system and method of the invention is to assess the longitudinal cross-sectional profile of a vessel lumen, for example, in the bronchi. The profile is obtained by aligning the light plane to the vessel's axis and recording the two cross-section curves generated.

Figure 8:
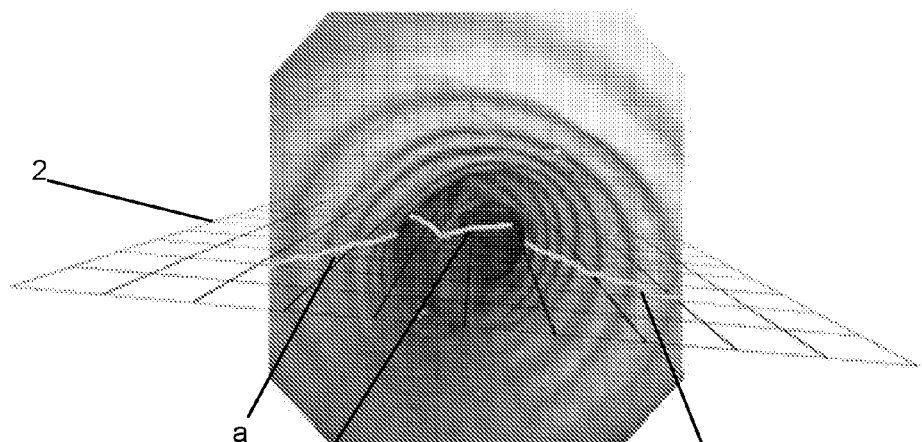
FIG. 8 shows an image of a human trachea imaged using a standard bronchoscope with superimposed features pertaining to a light plane that is aligned with the longitudinal cross-section of the trachea.

FIG. 8 shows an image of a human trachea imaged using a standard bronchoscope. Overlaid on the camera image is reticle 2, which lies in the generated light plane, which is aligned with the longitudinal cross-section of the trachea, and the curve segments a, b, and c created by intersection of the light plane with the walls of the trachea.

Figure 9:
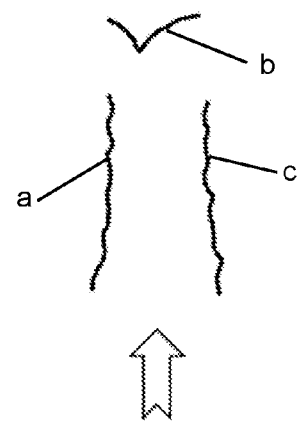
FIG. 9 shows the curve segments created by intersection of the light plane of FIG. 8 with the walls of the trachea, generating a longitudinal cross-section profile.

FIG. 9 shows the curve segments a, b, and c from FIG. 8 composing a quantitative longitudinal cross-section profile. The arrow illustrates the endoscopic view direction along the light plane. This separate view of the curve segments generates a non-distorted quantitative profile of the anatomical features in the endoscopic view and, for cases where in which the light plane is aligned with the longitudinal axis of a tubular structure, its longitudinal cross-section profile is provided.

Although embodiments of the invention have been described by way of illustration, it will be understood that the invention may be carried out with many variations, modifications, and adaptations, without exceeding the scope of the claims.

The invention claimed is:

1. A system for measuring 3D distances and dimensions of objects that are visible in endoscopic images, the system comprising:
   a) a flexible or rigid endoscopic device comprising visualization means;
   b) a conventional endoscopy system adapted to operate the endoscopic device and to obtain and display images gathered by the visualization means;
   c) a light plane generating module that is either integrated in a specific design for a dedicated measuring endoscopic device or a separate measurement device that can be attached to an existing endoscopic device, the light plane generating module comprising a light source and optical elements configured to generate a light plane that intersects objects of interest in the images; and
   d) a processor comprising: processing unit, dedicated software adapted to assign 3D coordinates to each pixel along the intersection curves of the light plane with objects in the images gathered by the visualization means, additional software is adapted to implement a graphical user interface (GUI) to make both Euclidian and geodesic measurements automatically or at user specified locations in the images, a pointing device, and a display adapted to present to the user of the system images acquired by the visualization means overlaid with graphics and text.

2. The system of claim 1 wherein some or all components of the processor are integrated into the conventional endoscopy system.

3. The system of claim 1 comprising a docking station for calibration of at least one of projection parameters of the visualization means, distortions of the visualization means, and light plane parameters.

4. The system of claim 1 wherein the dedicated software comprise programs that automatically perform at least one of the following operations:
   a) assigning 3D coordinates to each pixel along intersection curves of the light plane with the object;
   b) making Euclidean and geodesic measurements between at least two points overlaid by the user on an image displayed on the display;
   c) providing and displaying measurements of the Euclidean distance of gaps or diameters of holes and making geodesic measurements of curve segments to determine the diameter of objects seen in the images according to preprogrammed requests of the user or by pointing at a single point on the screen; and
   d) determining at least one of the projection parameters and distortions of the visualization means and light plane parameters from images recorded during a calibration process.

5. The system of claim 1 wherein the light plane generating module comprises one of the following:
   a) a light source and a single lens;
   b) a light source and an optical arrangement comprising at least one lens;
   c) a light source and a diffractive optical element (DOE);
   d) a light source and an optical arrangement comprising at least one DOE;
   e) a light source positioned at the proximal end of an optical fiber leading to a diffraction grating at the distal tip of the endoscope; and
   f) a light source positioned at the proximal end of an optical fiber leading to a lens at the distal tip of the endoscope.

6. The system of claim 1 wherein the light source is one of:
   a) a laser diode;
   b) a LED; and
   c) a light source that produces colored light.

7. The system of claim 1 wherein the light plane generating module is attached to the endoscopic device in one of the following ways:
   a) in a working channel of the endoscopic device; and
   b) in one channel of a two channel sheath wherein the insertion section of the endoscopic device is slid into the other channel; and
   c) a clip or a band attached to the outside of the distal tip of the endoscopic device.

8. The system of claim 1 wherein the light plane generating module is mounted below the objective lens of the visualization means in a pivoting arm configured to allow the distance between the focal point of the visualization means and the light plane to be changed.

9. The system of claim 1 comprising at least one of:
   a) multiple light planes;
   b) light planes having different line patterns or color coding.

10. The system of claim 1 comprising at least one of:
    a) a single light plane that is rotated or swept manually; and
    b) a single light plane that is rotated or swept in sync with an image acquisition camera.

11. The system of claim 10 wherein rotation or sweep is achieved by one of:
    a) MEMS mirrors;
    b) a rotation mechanism; and
    c) a combination of MEMS mirrors and a rotation mechanism.

12. The system of claim 1 wherein a reticle is superimposed on images from the visualization means displayed on the display.

13. A method for measuring 3D distances and dimensions of objects that are visible in endoscopic images, the method comprising the following steps:
    a) supplying a system according to claim 1;
    b) for a non-integrated add-on light plane generating module, mounting the light plane generating module at the tip of the endoscopic device and performing calibration;
    c) for an integrated or a non-integrated add-on light plane generating module, manipulating the endoscopic device such that the light plane coincides with the object to be measured;
    d) acquiring an image;
    e) selecting an image to be analyzed and using the GUI software to mark at least two points on the intersection curves of the light plane with the object;
    f) using the dedicated software module to measure and display the Euclidian distances between the marked points and, if the points lie on the same curve segment, to measure the geodesic distances along the segment;
    g) repeating steps e and f to measure additional objects if there is more than one object of interest in the image;
    h) recording the measurement data and related overlaid graphics if saving a permanent record of the measurements for later use is desired; and
    i) repeating steps e, f, g, and h for additional images.

14. The method of claim 13 wherein in step e only one point is marked on the image and step f further provides and displays measurements of the Euclidean distance of gaps or diameters of holes and geodesic measurements of curve segments to determine the diameter of objects seen in the images.

15. The method of claim 14 wherein the curve segments are displayed in a separate view, thereby generating a non-distorted quantitative profile of the objects in the endoscopic view and, for cases where in step c the light plane is aligned with the longitudinal axis of a tubular object, the longitudinal cross-section profile of the tubular object is provided.

16. The method of claim 14 wherein step d is replaced with on-line real-time automatic processing of video input during the procedure.

17. The method of claim 13 wherein in step e curve segments or gaps are automatically identified and analyzed by the dedicated software module of the processor and in step f the resulting measurements are displayed automatically, thereby automatically measuring geodesic lengths or diameters of tubular objects or gaps or diameters of holes.

18. The method of claim 13 wherein steps e to i are performed off-line after the procedure has been completed or on-line on the recently acquired image during the procedure.

19. The method of claim 13 wherein a spray of water, saline vapor, or the like is used to create haze to enable visualization of the laser plane.

20. The method of claim 13 wherein in step b the calibration is automatically performed by inserting the tip of the endoscopic device into a calibration docking station.

* * * * *